United States Patent [19]
Finkenaur et al.

[11] Patent Number: 5,427,778
[45] Date of Patent: Jun. 27, 1995

[54] GEL FORMULATIONS CONTAINING GROWTH FACTORS AND ACRYLAMIDE POLYMER

[75] Inventors: Amy L. Finkenaur, Somerville; Jonathan M. Cohen, Marlboro; Shalaby W. Shalaby, Lebanon, all of N.J.; Elisabeth A. Sandoval, Irvine, Calif.; Rao S. Bezwada, Whitehouse Station; Richard L. Kronenthal, Fairlawn, both of N.J.

[73] Assignee: Ethicon, Inc., Somerville, N.J.

[21] Appl. No.: 974,013

[22] Filed: Nov. 10, 1992

Related U.S. Application Data

[63] Continuation of Ser. No. 703,584, May 20, 1991, abandoned, which is a continuation of Ser. No. 233,483, Aug. 19, 1988, abandoned, Continuation-in-part of Ser. No. 98,816, Sep. 18, 1987, abandoned.

[51] Int. Cl.$^6$ .................. A61K 37/02; A61K 37/48
[52] U.S. Cl. ........................ 424/78.08; 424/94.1; 514/21
[58] Field of Search .............. 424/678, 78.08, 94.1, 424/94.6, 78.04; 514/2, 8, 12, 21

[56] References Cited

U.S. PATENT DOCUMENTS

| | | | |
|---|---|---|---|
| 4,100,271 | 7/1978 | Krezanoski et al. | 424/330 |
| 4,717,717 | 1/1988 | Finkenaur | 530/399 |
| 4,767,628 | 8/1988 | Hutchinson et al. | 424/426 |
| 4,806,523 | 2/1989 | Bentz et al. | 514/886 |

FOREIGN PATENT DOCUMENTS 1931080  12/1970  Germany.

*Primary Examiner*—Thurman K. Page
*Assistant Examiner*—Peter F. Kulkosky

[57] ABSTRACT

Gel formulations containing polypeptide growth factors having human mitogenic or angiogenic activity are provided. The gel formulations are useful for topical or incisional wound healing for cutaneous wounds, in the anterior chamber of the eye and other ophthalmic wound healing. The gel formulations also comprise a water soluble, pharmaceutically or ophthalmically compatible polymeric material for providing viscosity within various ranges determined by the application of the gel. The gel formulations provide controlled release and increased contact time of the growth factor to the wound site.

2 Claims, 3 Drawing Sheets

GEL FORMULATIONS CONTAINING GROWTH FACTORS AND ACRYLAMIDE POLYMER

BACKGROUND OF THE INVENTION

This application is a continuation of U.S. Ser. No. 703,584, filed May 20, 1991, now abandoned, which is continuation of U.S. Ser. No. 233,483, filed Aug. 19, 1988, abandoned, which is a continuation-in-part of U.S. Ser. No. 098,816, filed Sep. 18, 1987 now abandoned.

Throughout this disclosure, various publications, patents and patent applications are referenced. The disclosures of these publications, patents and applications in their entireties are hereby incorporated by reference into this disclosure in order to more fully describe the state of the art as known to those skilled therein as of the date of the invention described and claimed herein.

The present invention relates to gel formulations containing polypeptide growth factors having human mitogenic or angiogenic activity, in particular, epidermal growth factor.

The human polypeptide growth factors are molecules that regulate the growth of normal human cells. Many human polypeptide growth factors have been identified and their chemical structures determined. Those falling within this group are: epidermal growth factor (EGF), acidic and basic fibroblast growth factor (FGF), platelet derived growth factor (PDGF), transforming growth factor-a (TGF-a), transforming growth factor-ö (TGF-ö), insulin-like growth factors (IGF-I and IGF-II), and nerve growth factor (NGF). Because of their ability to stimulate cell growth, the human polypeptide growth factors have been described as being useful in stimulating the wound healing process.

One of the better characterized growth factors is epidermal growth factor. EGF is a 53 amino acid polypeptide growth factor that has mitogenic activity for a number of kinds of cells, including epithelial and mesenchymal cells. Variants of The naturally occurring EGF molecule have been reported, such as the 52 amino acid gamma-urogastrone. EGF has also been reported to have angiogenic activity. Epidermal growth factor exhibits epidermal growth promoting activity and gastric acid secretion inhibiting activity, and is therefore useful as a medicament. Epidermal growth factor has been reported as being useful for increasing the rate of healing wounds such as burns and incisions. Heretofore, there has not been provided a suitable delivery system for epidermal growth factor, as well as any other growth factor, for use in treating wounds. In particular, it is desirable to have a delivery system that controls the release of the growth factor to the wound and adheres to or maintains itself on the wound for an extended period of time in order to increase the contact time of the the growth factor to the wound. The present invention provides such delivery systems in the form of gels containing growth factors. Biocompatible gel materials may be used to deliver a growth factor to a wound and provide the advantages of a controlled profile of delivery and a moist environment for the wound.

SUMMARY OF THE INVENTION

The present invention provides aqueous gel formulations or viscous solutions for the controlled delivery of growth factors to a wound site. The formulation will depend on the type of application that is desired. Three different applications are intended, namely gels for topical or incisional wound healing, gels for healing wounds in the anterior chamber of the eye and low viscosity, aqueous formulations for those applications requiring a more fluid formulation having a higher water content.

An aqueous gel formulation for topical or incisional wound healing comprises an effective wound healing amount of a polypeptide growth factor having human mitogenic or angiogenic activity. Additionally, this formulation contains a water soluble, pharmaceutically acceptable polymeric material for providing viscosity within the range 1,000 to 12,000,000 cps at room temperature. An aqueous gel formulation for use in healing wounds in the anterior chamber of the eye comprises a water soluble ophthalmically compatible polymeric material for providing viscosity within the range 10,000 to 100,000 cps at room temperature. A low viscosity, aqueous formulation comprises a water soluble, pharmaceutically or ophthalmically compatible polymeric material for providing viscosity within the range 1 to 5,000 cps at room temperature. A preferred use for the low viscosity formulation is for ophthalmic wound healing. However, it may also be used for other types of wound healing, especially when used to soak a bandage placed on the wound.

The gel formulations of the present invention have the advantage of adhering to a wound and conforming to irregular body or wound contours. The gels may be applied directly to a wound site or in conjunction with a compliant porous or microporous substrate, for example in the form of a coating, to be applied to the wound site. Gels have the further advantages of having a high water content (which keeps the wound moist), the ability to absorb wound exudate, easy application to a wound and easy removal by washing. Gels have a cool feeling when applied to a wound and thus can increase patient comfort and acceptance of the formulation, especially on senstive wounds.

The gel formulations of the present invention also provide a controlled delivery system for growth factors on a wound site. Controlled delivery refers to drug release sufficient to maintain a therapeutic level over an extended period of time, such as up to 24 hours or more, preferably in the range of 1 to 12 hours. Increased contact time of growth factors, in particular EGF, at the wound site has been reported to be necessary to achieve a significant increase in the rate of wound healing. The present gel formulations increase the contact time of the growth factor at the wound site and provide a sustained release dosage form. This is an important advantage because it permits less frequent application of the formulation to the wound and thereby permits less disturbance of the wound and its cellular components, particularly at the different phases of mitosis.

DETAILED DESCRIPTION OF THE INVENTION

Figure 1:
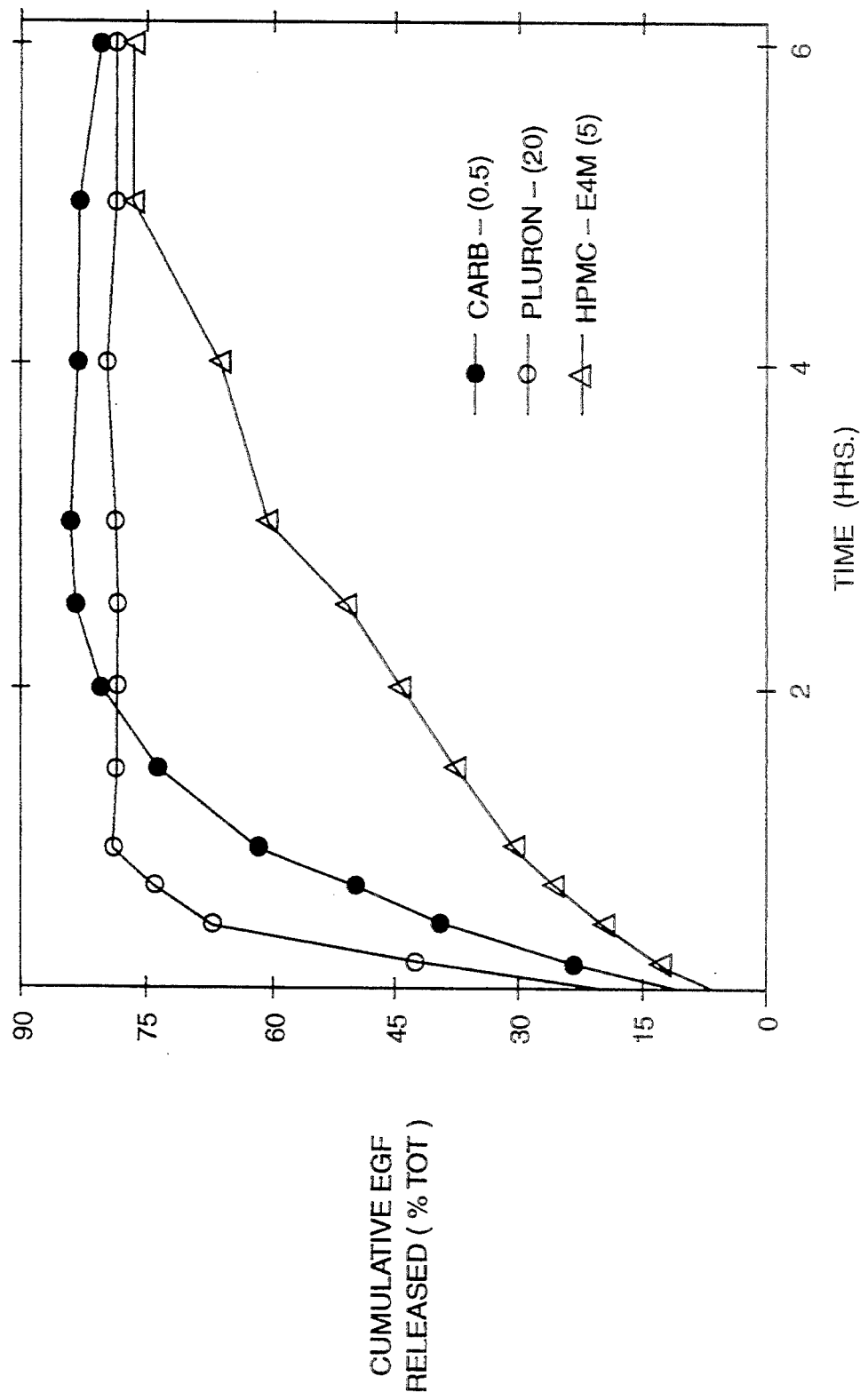
FIG. 1 depicts the percent release of EGF over time from gel formulations containing Carbopol 940, Pluronic F-127 and HPMC-E4M.

The aqueous gels of the present invention have different viscosities depending on the intended application of the gel. Viscosity is a measure of the resistance of a liquid to flow. It is defined as the ratio of the shearing stress to the rate of shearing. The shear stress is the resistance of the liquid to flow under the influence of an applied force, i.e., the molecular resistance within a body opposing an external force. The shear stress is defined as the ratio of the force to the area sheared. When a liquid is sheared, assuming laminar flow, the layers of the liquid move at different rates. The relative rate of motion of the layers is only one factor in the rate of shear. The other is the distance, or clearance between the shearing planes. Thus, shear rate is defined as the ratio of the velocity of the gel to the clearance. Viscosity has the dimensions of dynes/sec per $cm^2$. These dimensions are referred to as poise. The dimensions of viscosity referred to herein, unless otherwise indicated, are in centipoise (cps) as measured using a Brookfield viscometer. All viscosity values are at room temperature, e.g. 22°–25° C. unless otherwise indicated.

The polypeptide growth factors referred to herein are those having human mitogenic or angiogenic activity selected from the group consisting of EGF, acidic FGF, basic-FGF, PDGF, TGF-a, TGF-ö, angiogenin, NGF, IGF-I, IGF-II or mixtures thereof. It is contemplated that biologically active fragments or chemically synthesized derivatives of these growth factors may be used instead of the entire naturally occurring molecule. In addition to mitogenic activity, EGF, the FGF's, the TGF's and angiogenin are reported to have angiogenic activity. It is preferred that the growth factor be prepared by recombinant DNA techniques. As used herein, the phrase "growth factor" does not include the so called hematopoietic growth factors such as erythropoietin and the colony stimulating factors.

As used herein, human EGF refers to EGF having that polypeptide sequence or any substantial portion thereof set forth in Urdea, M. S. et al., Proc. Natl. Acad. Sci. (USA) 80:7461–7465 (1983). Human EGF also refers to any naturally occurring human EGF variant such as gamma-urogastrone. Epidermal growth factor, human epidermal growth factor and the other growth factors may be isolated from natural sources, produced using recombinant DNA techniques or prepared by chemical synthesis.

As used in this application, EGF is intended to include the class of polypeptides that have biological activity similar to that exhibited by the natural human EGF polypeptide as measured in recognized bioassays, such as the EGF receptor binding assay described in U.S. Pat. No. 4,717,717 and copending U.S. Ser. Number 096,455, filed concurrently herewith, and which have certain conserved amino acid residues and common positioning of disulfide bonds, as discussed by Carpenter et al. in "Epidermal Growth Factor, its receptor, and related proteins" Experimental Cell Research, 164:1–10 (1986) Thus, EGF includes the EGF produced by recombinant DNA techniques, mouse EGF isolated from the submaxillary glands of mice, rat EGF, and natural human epidermal growth factor, which may be isolated from human urine, and bioactive derivatives and related polypeptides of any of the foregoing, including precursors that are transformed into active epidermal growth factor in situ by proteolytic processing.

TGF-a, a 50 amino acid polypeptide is both mitogenic and has substantial sequence homology to epidermal growth factor, and appears to bind to and activate a common tyrosine kinase receptor. Because of its polypeptide nature, mitogenic activity and its substantial sequence homology with EGF, it is contemplated that TGF-a may also be useful in the gels of the present invention. Additionally, it is envisioned that any other polypeptide growth factor having mitogenic activity will also be useful in the gels of the present invention.

An effective wound healing amount of a polypeptide growth factor for use in the present invention may be within the range of about 0.01 to about 1,000 micrograms/ml. It is preferred that the growth factor concentration be about 1–500 micrograms/ml and more preferably 1–100 micrograms/ml. The gels of the present invention are capable of sustaining the release of the polypeptide growth factor. It is desirable that the gels have values for $T_{25}$ in the range 0.5–6.0 hours and $T_{50}$ in the range 2–12 hours. $T_{25}$ and $T_{50}$ are defined as the time (hrs) required, respectively, for 25% and 50% of the growth factor to be released from the dosage form and be detected in a receiving buffer in an in vitro diffusion system.

The gel forming materials of the present invention may be water soluble polymers capable of forming a viscous aqueous solution or non-water soluble, water swellable polymers (e.g. collagen), which can also form a viscous solution. Swellable polymers are those which absorb water rather than dissolve in water. Cross-linked forms of the polymers described herein may not be water soluble but may be water swellable. Therefore, cross-linked forms of the polymers are within the scope of the present invention. Cross-linking refers to covalently bonding polymer chains together with a bifunctional reagent such as glutaraldehyde. Also, it is understood by those skilled in the art that certain polymers may have to be used in the salt form or partially neutralized in order to be made water soluble. For example, hyaluronic acid is preferred to be used as sodium hyaluronate to provide suitable water solubility.

In the aqueous gel formulations for topical or incisional wound healing, the polymer may be selected from the group consisting of vinyl polymers, polyoxyethylene-polyoxypropylene copolymers, polysaccharides, proteins, poly (ethylene oxide), acrylamide polymers and derivatives or salts thereof. It is understood that poly (ethyleneoxide) includes polyethylene glycol. In the gel formulations for use in healing wounds in the anterior chamber of the eye, the polymers may be the same except that it is not preferred to use the polyoxyethylene- polyoxypropylene copolymers or poly(ethylene oxide). Also, for anterior chamber use, it is preferred that the polymer be biodegradable, i.e. it will break down into harmless constituents that can be drained from or metabolized in the anterior chamber. In the low viscosity, aqueous formulations for use in ophthalmic wound healing, the gel forming polymers may be the same as for topical or incisional wound healing, except that poly(ethylene oxide) is not preferred to be used.

The vinyl polymers (also known as substituted polyethylenes) useful in the present invention may be selected from the group consisting of polyacrylic acid, polymethacrylic acid, polyvinyl pyrrolidone and polyvinyl alcohol. The polysaccharides useful in the present invention may be selected from the group consisting of cellulose or cellulose derivatives, glycosaminoglycans, agar, pectin, alginic acid, dextran, starch, and chitosan. Starch occurs in two forms, a-amylose and amylopectin. The more water soluble a-amylose is preferred. The glycosaminoglycans may be selected from the group consisting of hyaluronic acid, chondroitin, chondroitin-4-sulfate, chondroitin-6-sulfate, dermatan sulfate, keratan sulfate, heparan sulfate and heparin. The glycosaminoglycans may be used to enhance wound healing in combination with any other gel forming polymer. The proteins useful in the present invention may be selected from the group consisting of collagen, gelatin and fibronectin. The acrylamide polymers may be polyacrylamide or polymethacrylamide polymers. Biocompatible polyacrylamide polymers are preferred.

In the gel formulation for topical or incisional wound healing, the viscosity may be within the range 1,000–12,000,000 cps at room temperature. It is preferred that the viscosity range be 50,000–2,000,000. In one embodiment of the present invention, the topical gel formulation may comprise 0.01–5% by weight polyacrylic acid having a molecular weight of about 450,000–4,000,000. In a preferred embodiment, the polyacrylic acid is present at 0.5–1.5% by weight and has a molecular weight of 2,000,000–4,000,000. The pH of the polyacrylic acid gel should be within the range 4.5–8 and more preferably in the range 6.5–7.5.

In another embodiment, the topical and incisional gel of the present invention may comprise 15–60% by weight of a polyoxyethylene-polyoxypropylene block copolymer having an average molecular weight of about 500–50,000. In a preferred embodiment, the block copolymer is present at 15–40% by weight and has a molecular weight in the range 1,000–15,000. The block copolymers used in the present invention are commonly known as Pluronicsc. Preferred Pluronics are Pluronic F88 and F127.

In a further embodiment, the topical or incisional gel may comprise 1 to 20% by weight of a cellulose derivative having a molecular weight of about 50,000 to 700,000. In a preferred embodiment, the cellulose derivative is present at 2–8% by weight and has a molecular weight in the range 80,000–240,000. Preferred cellulose derivatives are hydroxypropylmethyl cellulose (HPMC) and methyl cellulose (MC).

In a further embodiment, the topical and incisional gel may comprise 0.5–10% by weight of hyaluronic acid having a molecular weight in the range 500,000 to 8,000,000. In a preferred embodiment, the hyaluronic acid is present at 1.5–6.0% by weight and the molecular weight is greater than 1,000,000.

Acrylamide polymers may be useful for all types of wound healing, particularly in the anterior chamber of the eye. An absorbable acrylamide polymer, such as polyacrylamide, may be a good substitute for present carrier systems used in ophthalmic applications, such as hyaluronic acid. The acrylamide polymers may have a molecular weight in the range 1–13 million, preferably about 4–6 million. The weight percent of the acrylamide polymer in the gel may be 2–5%, preferably 3.5–4.5%. Substituted acrylamide polymers, such as methyl and alkyl substituted polymers are also within the scope of the present invention.

For use in the anterior chamber of the eye, an acrylamide gel delivery system has the following characteristics: any products of the dissolution or degradation of the delivery matrix are nontoxic and do not clog the trabecular mesh work; the gel is optically transparent; and the gel can be left in the anterior chamber without causing adverse clinical effects such as an unacceptable increase in occular pressure.

It will be readily apparent to one skilled in the art that the desired viscosity range may be achieved by varying the molecular weight and percent concentration of the polymer in the formulation. For example, a gel having a low viscosity may be achieved by using a low molecular weight of polymer or a lower percent concentration or a combination of the two. A high viscosity gel may be achieved by using a higher molecular weight polymer and a higher percent concentration. Intermediate viscosities may be achieved by varying the molecular weight and percent concentration accordingly.

In those gel formulations requiring lower viscosities than the topical and incisional gels, namely the formulation for use in healing wounds in the anterior chamber of the eye and the low viscosity solution for ophthalmic wound healing, the percent concentration of the polymer and its molecular weight may be varied to achieve the desired viscosity. For instance, in anterior chamber use, the gel may comprise a cellulose derivative that is 1–20% by weight and has a molecular weight in the range 80,000 to 240,000. The preferred range of concentration is 1–3%. In another embodiment for anterior chamber use the gel may comprise hyaluronic acid at a concentration of 0.5–5% by weight and a molecular weight of 500,000–8,000,000. It is preferred that the hyaluronic acid be present at a concentration of 0.5–2.0% and the molecular weight be 2,000,000–4,000,000. The preferred viscosity range for anterior chamber use is 10,000–100,000 cps.

The low viscosity solution may comprise 0.01–2.0% by weight polyacrylic acid having a molecular weight of about 100,000–4,000,000. In a preferred embodiment, the polymer is present at 0.05–0.5%. In another embodiment, this dilute viscous solution may comprise 2–40% by weight of a polyoxyethylene-polyoxypropylene copolymer having an average molecular weight of 500–500,000. Preferably, the concentration is 2–20% and the molecular weight is 1,000–15,000. Alternatively, the dilute viscous solution may comprise a cellulose derivative at 1–20% and having a molecular weight of about 80,000–240,000. It is preferred that the concentration be in the range of 1–10%. In a further embodiment, the dilute viscous solution may comprise 0.5–5.0% by weight hyaluronic acid having a molecular weight of about 500,000–8,000,000. Preferably, the concentration is 0.5–2.0% and the molecular weight is 1,000,000–6,000,000. If the dilute viscous solution is to be used as eye drops, it is preferred that the viscosity be in the range 1–100 cps. If it is used for other applications, such as soaking a bandage, then any viscosity in the range 1.0–5,000 will be suitable.

The cellulose derivatives used in the gels of the present invention are capable of stabilizing the polypeptide growth factors, in particular EGF, against loss of biological activity in an aqueous solution. Use of cellulose derivatives to stabilize growth factors against loss of biological activity is described in U.S. Pat. No. 4,717,717 and copending U.S. Ser. No. 096,455, filed concurrently herewith. The cellulose derivatives that are used in the present invention are water-soluble etherified cellulose derivatives such as alkyl celluloses, hydroxyalkyl celluloses and alkylhydroxyalkyl celluloses, for example methyl cellulose, hydroxyethyl cellulose, carboxymethyl cellulose, hydroxypropylmethyl cellulose and hydroxypropyl cellulose. Methyl cellulose and the hydroxyalkyl cellulose derivatives such as hydroxypropyl cellulose, hydroxyethyl cellulose and hydroxypropylmethyl cellulose are preferred.

The gels of the present invention may be lyophilized to provide a stable dosage form which can be reconstituted at the time of use. Lyophilized gels containing growth factors are described in U.S. Ser. No. 098,817, entitled "Stable Lyophilized Formulations containing Growth Factors," filed concurrently herewith.

The gel formulations of the present invention may be used to coat fibers of an absorbent gauze dressing to form a wound healing bandage which may then be placed on a wound. The low viscosity formulation is preferred for this use. The wound healing bandage may be prepared by soaking a gauze dressing with an aqueous gel solution containing a human polypeptide growth factor having mitogenic activity. The bandage can then be applied to the wound so that the coated fibers of the gauze contacts the wound and stimulate cell growth to increase the rate of wound healing.

The gels of the present invention are useful in eye drop formulations, ophthalmic irrigating solutions, salves for wound healing and the like. Wounds that may be healed using the compositions of the present invention are those which result from any accidental or medical injury which causes epithelial damage such as ophthalmic wounds, which result from corneal ulcers, radiokeratotomy, corneal transplants, epikeratophakia and other surgically induced wounds in the eye; and cutaneous wounds such as burn wounds, incisional wounds, donor site wounds from skin transplants, and ulcers (cutaneous, decubitis, venous stasis and diabetic). As used herein, ophthalmic wound healing includes anterior chamber wound healing as well as subconjunctival wound healing. The gels of the present invention may also be used for healing internal incisions as well as internal wounds such as gastric ulcers.

In those applications where the gel is applied to an internal or incisional wound, it is preferred that the gel forming polymer be degradable. The naturally occurring polymers are generally degradable. Examples of these are collagen, the glycosaminoglycans, gelatin and starch. The cellulosics are not degradable. The synthetic polymers such as the vinyl polymers are not degradable. The biodegradability of the polymers described herein is well known to those skilled in the art.

The following examples are presented to illustrate the subject invention. The invention is not be considered limited by these examples, but only by the appended claims.

EXAMPLE 1

Polyacrylic Acid Gels

Polyacrylic acid gels (Carbopolc) were prepared according to the present invention. Preferred grades of polyacrylic acid are those referred to as Carbopol 934 P and 940 at concentrations of 0.02–1.5%. Higher concentrations of polyacrylic acid lower the release rate of the EGF. Viscosities of polyacrylic acids are generally stable between pH 6–10, preferably in the pH range 6.5–7.5.

The following ingredients were combined in a 4 liter beaker: 6.3 g methyl paraben, 0.7 g propylparaben and 177.5 g mannitol in 3500 ml water. This solution was mixed with a paddle type mixer until the solids dissolved. Polyacrylic acid (17.5 g, Carbopol 940, BF Goodrich) was sieved through a 40 mesh screen into the solution while it was mixed at 1,000 rpm. This dispersed and swelled the polyacrylic acid particles. The solution was neutralized to pH 7.0 by the addition of 7.6 grams solid NaOH in 10% solution. A 900 g portion of this gel was removed from the batch and autoclaved to provide a sterile gel. The remainder of the procedure was performed in a class 100 area. A stock solution of EGF at 1.18 milligrams/ml (12 ml) was filtered through a 0.22 micrometer filter into a sterile tube and the filter was washed with a 5 ml aliquot of water into the same tube. The contents of the tube were added to the gel by syringe. The gel was mixed thoroughly with a paddle type mixer to uniformly disperse the EGF. The gel was placed in an autoclaved pressure vessel. Nitrogen was used to force the gel to flow out of the pressure vessel into 10 ml syringes via a sterile piece of tubing. Samples were tested for activity and shown to contain 15.6 micrograms of EGF/ml. The samples were free from microorganisms in a 10 g sample. The viscosity of the gels prepared ranged from about 490,000 to about 520,000 cps. This gel formulation was used in a pig and guinea pig partial thickness skin excision model and the gel showed an enhanced rate and quality of wound healing in these animals.

EXAMPLE 2

Pluronic Gel Formulations

Polyoxyethylene-polyoxypropylene block copolymers (Pluronicsc) have great potential for use in topical drug delivery systems, since they exhibit reverse thermal gelation behavior and they have good drug release characteristics as well as low toxicity. Low molecular weight Pluronic polyols do not form gels at any concentration in water. Pluronic F-68 forms a gel at a minimum concentration of 50–60% at room temperature. Pluronic F-68 forms a gel at 40% at room temperature and Pluronic F-108 forms a gel at 30% concentration. Pluronic F-127 forms a gel at only 20% concentration in water at 25° C. Pluronic gels of F-68, F-88, F-108 and F-127 may be used for controlled delivery of EGF for burns and other donor site dosage forms. The gel should be isotonic and it is preferred that the pH be in the range 6–8, and more preferably 6.5–7.5.

An interesting property of the Pluronic gels is their ability to gel as a function of temperature and polymer concentration. Gels are formed as the Pluronic solution is warmed. Thus, the gel is a low viscosity aqueous solution at room temperature, but when it contacts the human body and is warmed by body temperature the viscosity increases and the solution gels. EGF may be combined with the Pluronic in the liquid state and applied to the wound. At this point, gelation would occur which would effectively reduce the rate of EGF released to the wound. This permits prolonged contact time between EGF and the epithelium of the wound. The gel could be applied as a liquid or in conjunction with a dressing (soaked in the liquid) to give mechanical support. Advantages of using Pluronic gels include the availability of filtration methods for sterilization of these gels and the wound would be in prolonged contact with the EGF.

A Pluronic F-127 gel containing EGF was prepared by mixing the following: 1.8 g sodium phosphate monohydrate, 5.48 g disodium phosphate heptahydrate and 40.9 g mannitol were combined in 1,000 ml of distilled water. The pH was adjusted to 7.0 and the solution was cooled to 4° C. Pluronic F-127 (200 g) (BASF) was added to the cooled solution gradually while mixing with a paddle type mixer. The solution was mixed for about 30 minutes and then placed at 4° C. overnight. EGF in an aqueous solution may be added to the solution before the gel is made or may be mixed after dissolving the Pluronic F-127 in solution. To obtain an EGF concentration of 100 micrograms/ml, 1.812 ml of an EGF solution (1.38mg/ml) was added to 23.188 g of 20% Pluronic F-127 gel. The solution is very liquid like. The viscosity of the solution increased as it was warmed to 35° C., as can be seen in Table 1.

TABLE 1

| Temperature °C. | Viscosity (cps, 0.5 rpm) |
| --- | --- |
| 0–16 | Not detectable |
| 18 | 4,000 |
| 19 | 250,000 |
| 21 | 500,000 |
| 28 | 655,000 |
| 30 | 685,000 |
| 37 | 650,000 |

Additional Pluronic formulations were prepared which had viscosities of 1,000,000 to 12,000,000. The release kinetics of a formulation ($11.5 \times 10^6$ cps) was tested and it was noted that the 85% of the EGF was released from the formulation within one hour.

EXAMPLE 3

HPMC Gel Formulations

Several HPMC gels were prepared. The gels were made from very low molecular weight to high molecular weight HPMC. Preferably the molecular weight range is from 80,000–240,000. With very low molecular weight polymers (Methocelc E15LV), as much as 10–20% HPMC is required to form a gel. For very high molecular weight polymers (Methocelc K100M), gels can be made from a 1–3% solution. Gels were made with different grades and different concentrations to study the release kinetics. The pH was adjusted to 7.2 for each gel. The rate of EGF release was proportional to the viscosity of the soluble gel.

In a 1,500 ml beaker were placed 0.83 g sodium phosphate monohydrate, 7.24 g disodium phosphate heptahydrate, 6.22 g NaCl and 500 ml sterile water for irrigation. The mixture was stirred magnetically to dissolve the solids and the pH was adjusted to 7.2. The solution was heated to 80° C. while stirring and 30.0 g of HPMC (Methocelc K100M; Dow) was added through a 40 mesh sieve. It was removed from the heat and stirred for 10 more minutes. The remaining water 500 g was added as ice. Stirring was performed by hand as the mixture became more viscous. It was allowed to cool to room temperature and then cooled to 4° C. overnight. A 130 g portion was removed and mixed with 13.4 ml of a 1.12mg/ml sterile solution of EGF with a paddle mixer to obtain an EGF concentration of 104 micrograms/ml.

The gels prepared had viscosities that ranged from 54,000 to 950,000 cps at room temperature. The release of the EGF from the various HPMC gel formulations prepared is set forth in Table 2.

TABLE 2

| | Brookfield Viscosity (CPS) | | |
| --- | --- | --- | --- |
| Sample | 25° C. | 37° C. | Release of EGF |
| 2085-91-1 E4M 4% | $112 \times 10^3$ | $102 \times 10^3$ | 75% in 5 hours |
| 2085-92-2 E4M 5% | $274 \times 10^3$ | $300 \times 10^3$ | 75% in 5 hours |
| 2085-92-2 E4M 6% | $652 \times 10^3$ | $946 \times 10^3$ | 50% in 5 hours |
| 2085-91-2 F4M 4% | $112 \times 10^3$ | $286 \times 10^3$ | 75% in 5 hours |
| 2085-93 K15M 3% | $102 \times 10^3$ | $70 \times 10^3$ | 75% in 5 hours |
| 2085-91-3 K4M 4% | $92 \times 10^3$ | $54 \times 10^3$ | 75% in 5 hours |

EXAMPLE 4

Hyaluronic Acid Gel Formulations

Hyaluronic acid (HA) is one of the mucopolysaccharides having a straight chain structure consisting of the repetition of a disaccharide unit of N-acetylglucosamine and glucuronic acid. HA is found in nature, in microorganisms and in the skin and connective tissue of humans and other animals. Molecular weights of HA are within the range of 50,000–8,000,000 depending on source, methods of preparation and method of determination. Highly viscous solutions can be made by dissolving HA in water. Viscous solutions of HA have lubricating properties and an excellent moisturizing effect. It is found in the synovial fluid of joints, vitreous body of the eyeball, umbilical cord, skin, blood vessels and cartilage. It works remarkably well as a lubricant and shock absorbing agent and this is probably due to its water retaining ability and its affinity for linking it to certain specific proteins. It is considered to be a very safe molecule for use internally in the human body. Thus, it may be used in internal wound healing such as healing of joints or in the anterior chamber of the eye. A 1% solution of sodium hyaluronate (molecular weight 4,000,000;MedChem) was formulated with EGF to obtain a concentration of 100 micrograms/ml. The viscosity of the 1% HA solution was 44,000 cps. An HA/EGF formulation prepared according to the present invention has been demonstrated to stimulate reendothelialization in the anterior chamber of the eye.

EXAMPLE 5

Kinetics of Release of EGF from Dosage Forms

The effectiveness of each dosage form to sustain the release of EGF in an in vitro diffusion cell system was evaluated and values for $T_{25}$ and $T_{50}$ were determined. EGF is released as a result of both the diffusion of the EGF from the gel and the dissolution of the gel matrix. Taking these two processes as the likely mechanisms by which EGF will be bioavailable in vivo, HPMC gels sustain the release of EGF with the highest values, with $T_{25}$ and $T_{50}$ values of 1.2 and 5.9, respectively. Results indicated that the molecular structure of the polymer was more important than the concentration of the polymer in prolonging T values. Gels that were made in salt free media (distilled water) and studied under standing conditions yielded low T values. This may be a result of a combination of faster dissolution and lower viscosity of salt-free gels. Therefore, it is preferred that the gels of the present invention not be salt-free. It is envisioned that the T values for the gels of the present invention may be increased by modifying the polymer such as by introduction of hydrophobic or hydrophilic side chains, ion pair groups, metal ions, cross-linking agents, affinity groups for EGF to control the release of EGF from the resulting product form.

Table 3 summarizes the kinetic data of the release of EGF from dosage forms. Referring to the Table, the different letters following HPMC refer to the percent substitution in the polymer. For example, K=2208 or 22% methylated and 8% hydroxy-propyl substituted; F=2906; and E=2910. The numerical value following the letter (i.e., the number 100 following the K) refers to the viscosity of a 2% solution in water in thousands cps. AQ refers to gels made in salt-free solution. All other gels were made in phosphate buffered saline (PBS) at a pH of approximately 7.0. T values are in hours. FIG. 1 graphically depicts some of the data of Table 3.

TABLE 3

Summary of Kinetic Data of the Release of EGF from Dosage Forms

| Polymer | | Viscosity (cps) | $T_{25}$ | $T_{50}$ |
|---|---|---|---|---|
| HPMC K100M | 1% | — | 0.0854 | 1.000 |
| (mw 240,000) | 2% | $287 \times 10^3$ | 0.4687 | 1.9172 |
| | 3.5% | $116 \times 10^6$ | 1.2270 | 5.8528 |
| | 4.0% | — | 0.8536 | 4.1386 |
| | 5.0% | $3.07 \times 10^6$ | 0.8807 | 3.5808 |
| HPMC K-15M | 3% | $122 \times 10^3$ | 0.857 | 2.0635 |
| (mw 120,000) | 4AQ% | $331 \times 10^3$ | 0.2727 | 1.6900 |
| HPMC K-4M | 4% | $96 \times 10^3$ | 1.0476 | 2.6349 |
| (mw 86,000) | | | | |
| HPMC F-4M | 4% | $122 \times 10^3$ | 0.7619 | 1.8730 |
| (mw 86,000) | | | | |
| HPMC E-4M | 4% | $128 \times 10^3$ | 1.0159 | 2.2657 |
| (mw 86,000) | 5% | $312 \times 10^3$ | 0.8615 | 1.8462 |
| HPMC E-4M | 5AQ% | $240 \times 10^3$ | 0.3211 | 1.6044 |
| (mw 86,000) | 6AQ% | $680 \times 10^3$ | 0.6944 | 3.0040 |
| Carbopol 934P | 0.5% | $494 \times 10^3$ | 0.2727 | 0.7300 |
| (mw $3 \times 10^6$) | | | | |
| Pluronic F-127 | 20% | $1.1 \times 10^6$ | 0.1936 | 0.3548 |
| (mw 12,000) | | | | |

EXAMPLE 6

Polyacrylamide Gel Formulations

Polyacrylamide/EGF gel formulations were prepared using the polyacrylamides CyanamerT N-300 and CyanamerT N-300 LMW (both commercially prepared by American Cyanamid). The CyanamerT N-300 had a molecular weight of about 5-6 million and the CyanamerT N-300 LMW had a molecular weight of about 13 million.

Polyacrylamide gels of the following compositions were prepared by adding the polyacrylamide polymer to the premixed salt solutions. These gels were then used for testing the release of EGF.

TABLE 4

| | % Concentration by weight | |
|---|---|---|
| Composition | 2085-140A | 2085-140B |
| Cyanamer N-300 | 4.0 | — |
| Cyanamer N-300 LMW | — | 4.0 |
| Sodium chloride | 0.049 | 0.049 |
| Potassium chloride | 0.075 | 0.075 |
| Calcium chloride | 0.048 | 0.048 |
| Magnesium chloride | 0.080 | 0.080 |
| Sodium acetate | 0.890 | 0.890 |
| Sodium citrate dehydrate | 0.170 | 0.170 |
| Sterile water | 94.688 | 94.688 |
| Viscosity, cps. | $552 \times 10^3$ | $132 \times 10^3$ |

Figure 2:
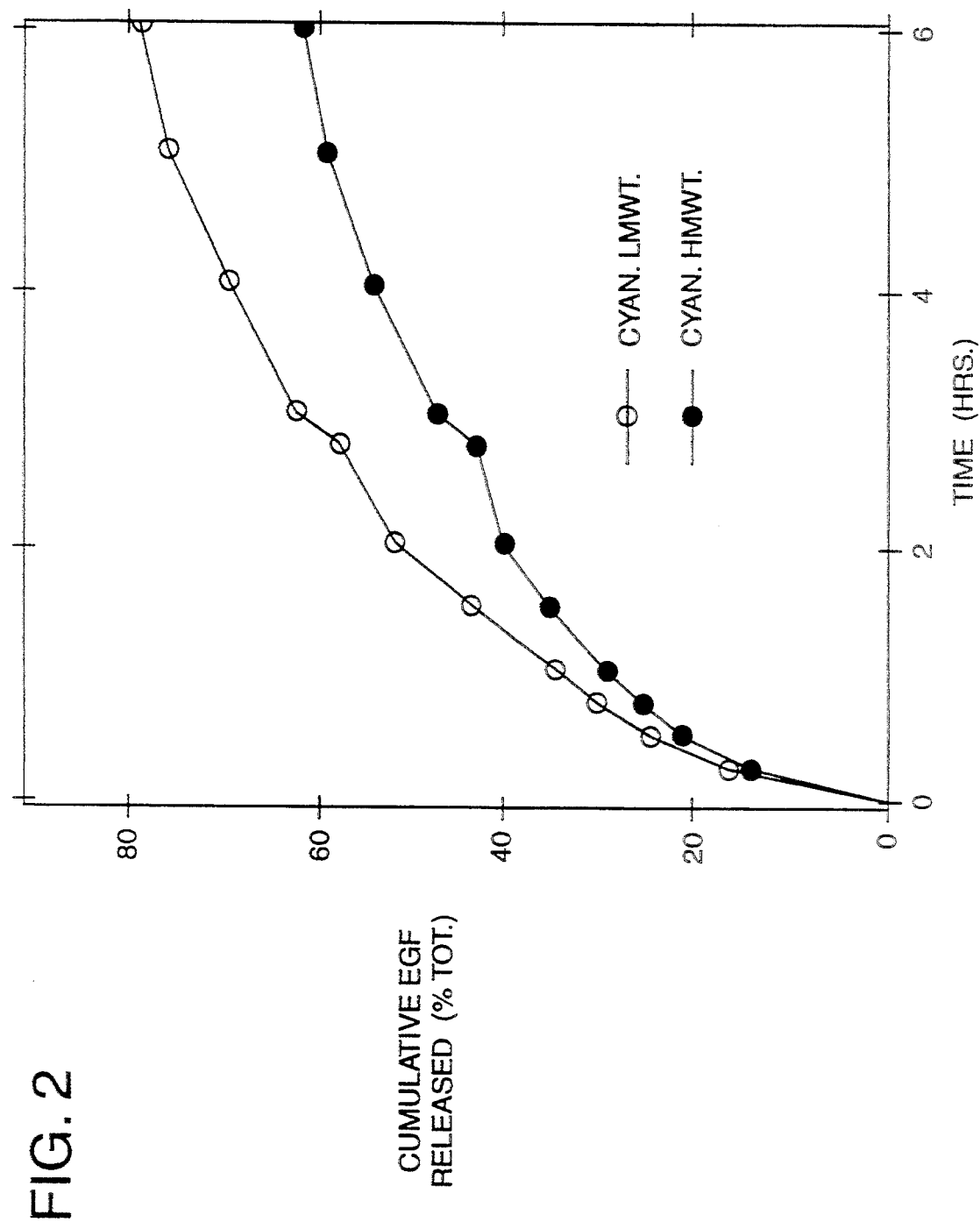
FIG. 2 depicts the percent release of EGF over time from polyacrylamide gel formulations.

To 1.809 grams of polyacrylamide gel of Cyanamer N-300 (2085-140A), 72.4 microliters of a mixture of $^{125}$I-EGF and EGF were added and mixed in two 3 milliliter syringes. 300–400 milligrams of this gel was placed in the donor side of a Franz diffusion cell. At predetermined time intervals, 50 microliter aliquots of the receiving buffer was counted on a gamma counter. The receiving buffer consisted of 3.5 milliliters PBS, pH7.2 containing 0.4% BSA (bovine serum albumin) and 0.02% sodium azide. The results were expressed in % EGF released based on the total count added to the gel (see FIG. 2). Similarly, to 1.11 grams of polyacrylamide gel of Cyanamer N-300 LMW (2085-140B), 44.5 microliters of a mixture of $^{125}$I-EGF and EGF were added, and the release of EGF was examined (see FIG. 2).

Another polyacrylamide gel (2085-138C) was prepared having the following formulation.

TABLE 5

| Composition | 2085-138C |
|---|---|
| Cyanamer N-300 | 7.0 g |
| Thimerosal | 0.2 g |
| Sterile water | 192.8 g |
| viscosity | $258 \times 10^3$ |
| pH | 7.54 |

The 2085-138C gel was used to prepare a gel containing EGF at 10 micrograms/ml. Five grams of the 2085-138C gel was weighed into an 8 ml serum vial and 50 micrograms of 1 mg/ml EGF (protein assay 1.41 mg/ml) was added.

Figure 3:
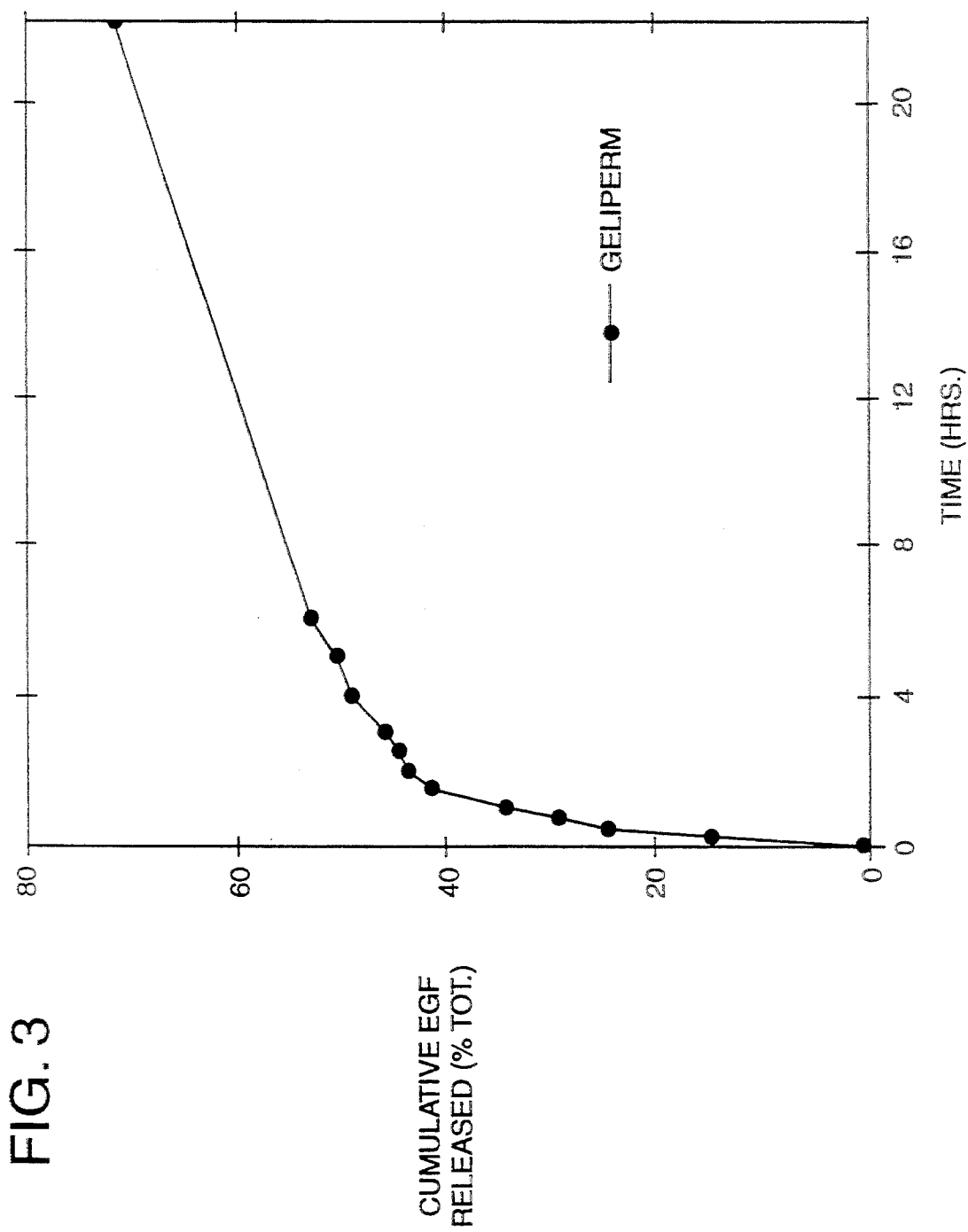
FIG. 3 depicts the percent release of EGF over time from a polyacrylamide/agar GelipermT wound dressing.

EGF was coated onto a wound dressing and favorable release characteristics were obtained. The wound dressing was a gel film made of polyacrylamide/agar (GelipermT, Geistlich-Pharma; Wolhusen, Switzerland.) The dressing was coated with EGF by soaking the dressing with an aqueous solution of EGF. About 70% of the EGF was released from the dressing in about 24 hours. FIG. 3 depicts the release of EGF from the dressing over time.

The invention has been described herein with reference to certain preferred embodiments and examples. It is readily apparent that obvious variations may appear to those skilled in the art. In particular, one skilled in the art may be able to vary the molecular weights and percent concentrations of the various polymers to achieve the desired viscosities. Also, one skilled in the art may be able to substitute different polymers or growth factors for those recited herein. Since obvious variations will appear to those skilled in the art, the invention is not to be considered limited thereto but only by the claims which follow.

What is claimed is:

1. An aqueous gel formulation for topical or incisional wound healing, comprising:
   a) an effective wound healing amount of a growth factor selected from the group consisting of EGF, acidic FGF, basic FGF, PDGF, TGF-alpha, TGF-beta, NGF, IGF-I, IGF-II, angiogenin, and mixtures thereof; and
   b) an agent for providing viscosity within the range 50,000 to 2,000,000 cps at room temperature, said agent consisting essentially of an acrylamide polymer, said agent consisting essentially of an acrylamide polymer.

2. A method for treating a topical or incisional wound comprising applying to the wound a composition of claim 1.

* * * * *